United States Patent
Doubler et al.

(10) Patent No.: US 6,299,648 B1
(45) Date of Patent: Oct. 9, 2001

(54) LOCKING HIP PROSTHESIS

(75) Inventors: Robert L. Doubler, Ida, MI (US); John E. Hammill, Sr., Rossford, OH (US)

(73) Assignee: Hammill Manufacturing Co., Toldeo, OH (US)

( * ) Notice: Subject to any disclaimer, the term of this patent is extended or adjusted under 35 U.S.C. 154(b) by 0 days.

(21) Appl. No.: 09/527,180

(22) Filed: Mar. 17, 2000

(51) Int. Cl.$^7$ .................................................. A61F 2/32
(52) U.S. Cl. ...................... 623/23.18; 623/22.42
(58) Field of Search ..................... 623/22.42, 22.43, 623/22.41, 22.4, 22.45, 28.15, 23.18, 23.23

(56) References Cited

U.S. PATENT DOCUMENTS

| | | |
|---|---|---|
| 2,785,673 | 3/1957 | Anderson . |
| 3,067,740 | 12/1962 | Haboush . |
| 3,820,167 | 6/1974 | Sivash . |
| 3,894,297 | 7/1975 | Mittelmeier et al. . |
| 3,987,499 | 10/1976 | Scharbach et al. . |
| 4,003,095 | 1/1977 | Gristina . |
| 4,004,300 | 1/1977 | English . |
| 4,051,559 | 10/1977 | Pifferi . |
| 4,141,088 | 2/1979 | Treace et al. . |
| 4,167,047 | 9/1979 | Grundei et al. . |
| 4,549,319 | 10/1985 | Meyer . |
| 4,550,448 | 11/1985 | Kenna . |
| 4,846,839 | 7/1989 | Noiles . |
| 4,851,007 | 7/1989 | Gray . |
| 4,878,917 | 11/1989 | Kranz et al. . |
| 4,919,678 | 4/1990 | Kranz et al. . |
| 4,963,155 | 10/1990 | Lazzeri et al. . |
| 5,002,578 | 3/1991 | Luman . |
| 5,002,581 | 3/1991 | Paxson et al. . |
| 5,080,685 | 1/1992 | Boleskey et al. . |
| 5,181,928 | 1/1993 | Bolesky et al. . |
| 5,192,324 | 3/1993 | Kenna . |
| 5,370,706 | 12/1994 | Bolesky et al. . |
| 5,397,360 | 3/1995 | Cohen et al. . |
| 5,441,537 | 8/1995 | Kenna . |
| 5,509,935 | 4/1996 | Fosco et al. . |
| 5,653,765 | 8/1997 | McTighe et al. . |
| 5,702,480 | 12/1997 | Kropf et al. . |
| 5,725,592 | 3/1998 | White et al. . |
| 5,876,459 | 3/1999 | Powell . |
| 5,906,644 | 5/1999 | Powell . |

*Primary Examiner*—David J Isabella
(74) *Attorney, Agent, or Firm*—McHale & Slavin

(57) ABSTRACT

A modular prosthesis has an intramedullary rod element which is to be inserted in a bone. The rod has a shaped proximal portion which is telescoped into one end of a bore in the trochanter element. The mating surfaces of the shaped rod and the trochanter bore form a rotationally immovable connection. A neck element is telescoped into the other end of the trochanter bore permitting rotational adjustment. All the elements are locked together by a bolt through the neck and rod.

7 Claims, 4 Drawing Sheets

LOCKING HIP PROSTHESIS

FIELD OF THE INVENTION

This invention relates to the surgical field of joint replacement, particularly to a modular artificial joint having three elements which replace the natural hip, and most particularly to the connection between the intramedullary rod and the other parts of the prosthesis.

BACKGROUND OF THE INVENTION

In replacing a hip joint, the head of the femur is removed along with the ball. The femur is shaped and prepared for receiving the prosthesis so that the artificial joint will closely approximate the natural hip.

The modular artificial joint has three elements which replace the natural hip. The intramedullary rod is inserted into the end of the femur. The entire prosthesis is supported by this connection between the rod and the femur. The upper portion of the rod which extends out of the femur is fitted into a trochanter element which is shaped like the removed broad head of the femur which it replaces. This element, along with the rod, is used to adjust the length of the prosthesis to approximate the natural length of the femur. A neck element is inserted into the trochanter element and carries an angular extension onto which the ball joint will be fixed. All these elements have a central bore and are permanently secured together by a bolt which is inserted into the neck element, extends through the trochanter element, and is threaded into the upper end of the rod. In some cases, the intramedullary rod may be attached to the bone with bone cement while, in other cases the cement is omitted.

When the cement is omitted, the placement and fixation of the intramedullary rod becomes more critical to pain free usage of the prosthesis. Further, it is most important that the intramedullary rod not be disturbed after insertion since this would corrupt the union between the rod and the interior of the femur.

In order to maintain the original union between the femur and the intramedullary rod, modular prosthesis have been developed to allow rotational adjustment of the several parts or elements about the rod during the placement of the prosthesis to more closely reproduce the natural structure of the hip. The modular concept also allows the selection of different sized elements, before or during surgery, to more closely approximate the natural joint.

With the advantage of flexibility gained by modular prosthesis, there comes the requirement that there be no movement between the several parts or elements after implantation. These movements may cause misalignment of the joint resulting in increased pain, trauma to the joint and, even, dislocation of the joint.

DESCRIPTION OF THE PRIOR ART

The prior art is replete with artificial prosthesis and hip joints, in particular.

Illustrative of the state of the art are U.S. Pat. No. 5,876,459 and U.S. Pat. No. 5,506,644 to Powell which disclose modular hip joints having a stem, one end of which is inserted in the intramedullary canal. The other end of the stem is tapered to fit within a second, neck, element. The neck ultimately supports the ball joint. A sleeve element is placed over the junction of the first two elements. All three elements are rotationally movable relative to each other. A bolt is driven through the bore of the neck and stem deforming a portion of the interconnected elements for a friction fit between the neck and the stem. These prior art patents disclose that the sleeve may have a polygonal shaped bore with the articulating elements having corresponding shaped portions. The interconnected elements of these hip joints do not form a static lock between each other but require a deformation of one or more elements before a friction fit is established. The deformation and friction fit is between the stem and the neck rather than the sleeve and the stem.

U.S. Pat. No. 5,653,765, to McTighe et al discloses a modular hip joint with a stem, an intermediate shoulder portion, and a proximal shoulder piece which attaches to the ball. The stem and the intermediate shoulder portion have interengaging teeth on the corresponding ends of each by which they are connected. This end-to-end connection allows for rotational movement of the elements relative to each other. The proximal shoulder piece and the intermediate shoulder piece also have an end-to-end toothed connection for rotational adjustment. This construction has two movable end-to-end connections which provide good flexibility for rotation of the elements but have small surface areas of fixation to each other limited to the surfaces of the interengaged teeth.

SUMMARY OF THE INVENTION

In the instant invention a modular prosthesis is taught which has an intramedullary rod element which is to be inserted in a bone. The rod has a shaped proximal portion which is telescoped into one end of a bore in the trochanter element. The mating surfaces of the shaped rod and the trochanter bore form a rotationally immovable connection. A neck element is telescoped into the other end of the trochanter bore permitting rotational adjustment. All the elements are locked together by a bolt through the neck and rod.

In a particularly preferred embodiment of the instant invention a modular prosthesis is taught for use as a hip replacement which comprises an intramedullary rod, a trochanter and a neck, said intramedullary rod having a distal end adapted for insertion into the intramedullary canal of the femur and a proximal end, said proximal end having a circumference with opposite planar surfaces joined by curved surfaces, said proximal end having a screw threaded blind bore along the longitudinal axis of said intramedullary rod, said trochanter having a narrow distal end and a larger proximal end with a through bore from said distal end to said proximal end, said proximal end of said through bore having a smooth circumference, said distal end of said through bore having a circumference with opposite planar sides joined by curved surfaces, said circumference of said trochanter bore and said circumference of said proximal end of said intramedullary rod adapted to telescope together forming a rotationally secure connection, said neck having a distal end adapted to be inserted into the proximal end of said through bore of said trochanter, said distal end of said neck having a smooth circumference, said distal end of said neck and said proximal end of said through bore in said trochanter adapted to telescope together forming a rotationally adjustable connection, said neck having a through bore, said proximal end of said through bore having a countersunk bore, said distal end of said through bore adapted to telescope over the proximal end of said intramedullary rod, and a screw threaded bolt adapted to be disposed in said countersunk bore and threadably engaged with said screw threads in said proximal end of said intramedullary rod forming a locked integral prosthesis.

Accordingly, it is an objective of the instant invention to provide a hip joint with an intramedullary rod element which is connected with the trochanter element in such a manner as to prevent any rotational movement between the elements. Rotational movement, in this context, refers to the turning of either element in a plane normal to the common longitudinal axis of the elements.

It is a further objective of the instant invention to provide a connection between the trochanter element and the intramedullary rod in such a manner as to limit the combined length of the elements.

It is a further objective of the instant invention to provide the intramedullary rod with a fluted exterior surface for increasing the surface area of the junction between the rod and the intramedullary canal of the femur.

It is yet another objective of the instant invention to provide a slot through the end of the intramedullary rod to increase the accommodation of the rod with the interior of the intramedullary canal of the femur.

It is a still further objective of the invention provide a connection between the neck element and the trochanter element that permits rotational adjustment and limits the length of the combined elements.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Figure 1:
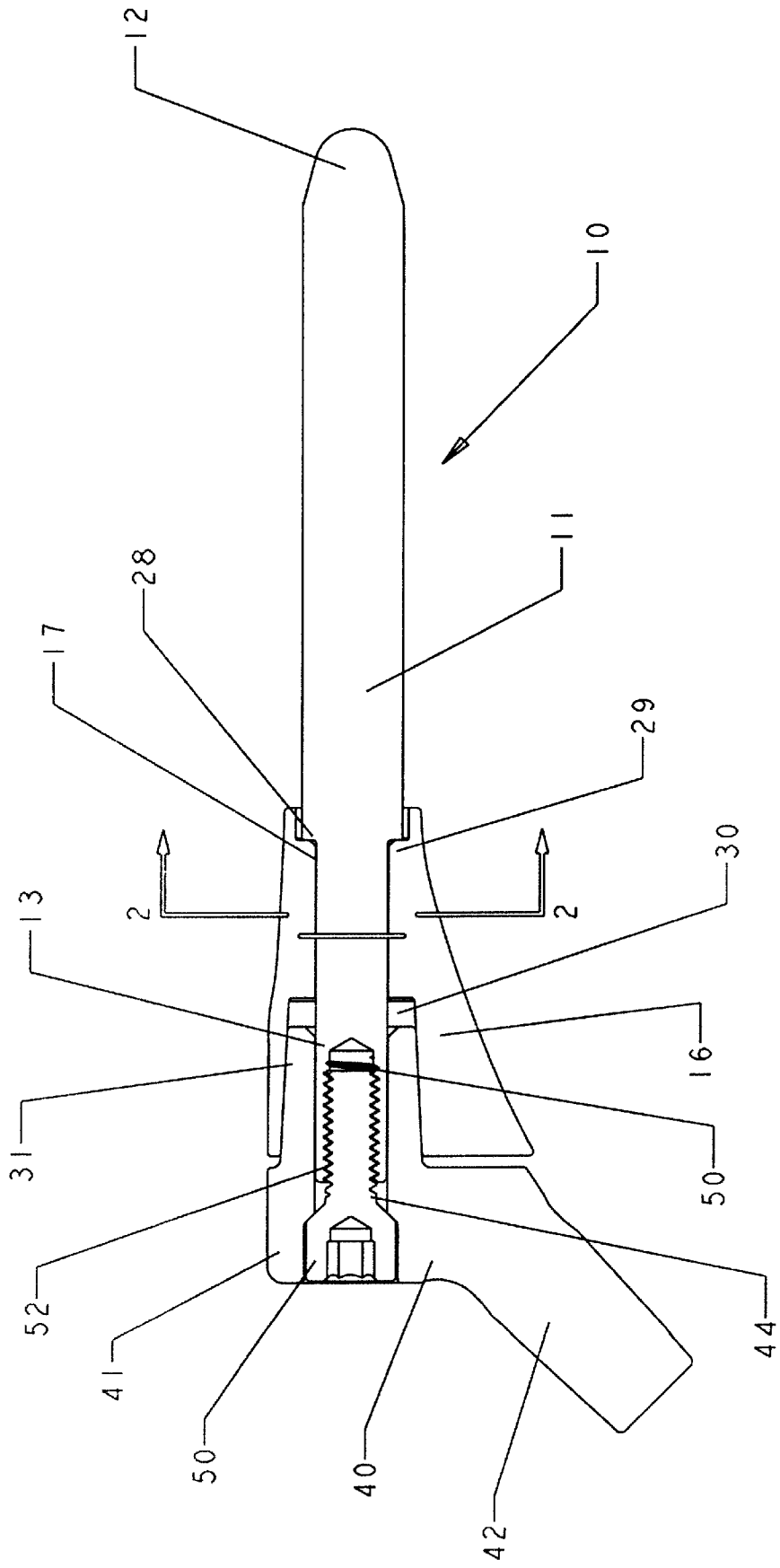
FIG. 1 is a cross section of one embodiment of the prosthesis of this invention.
Figure 4:
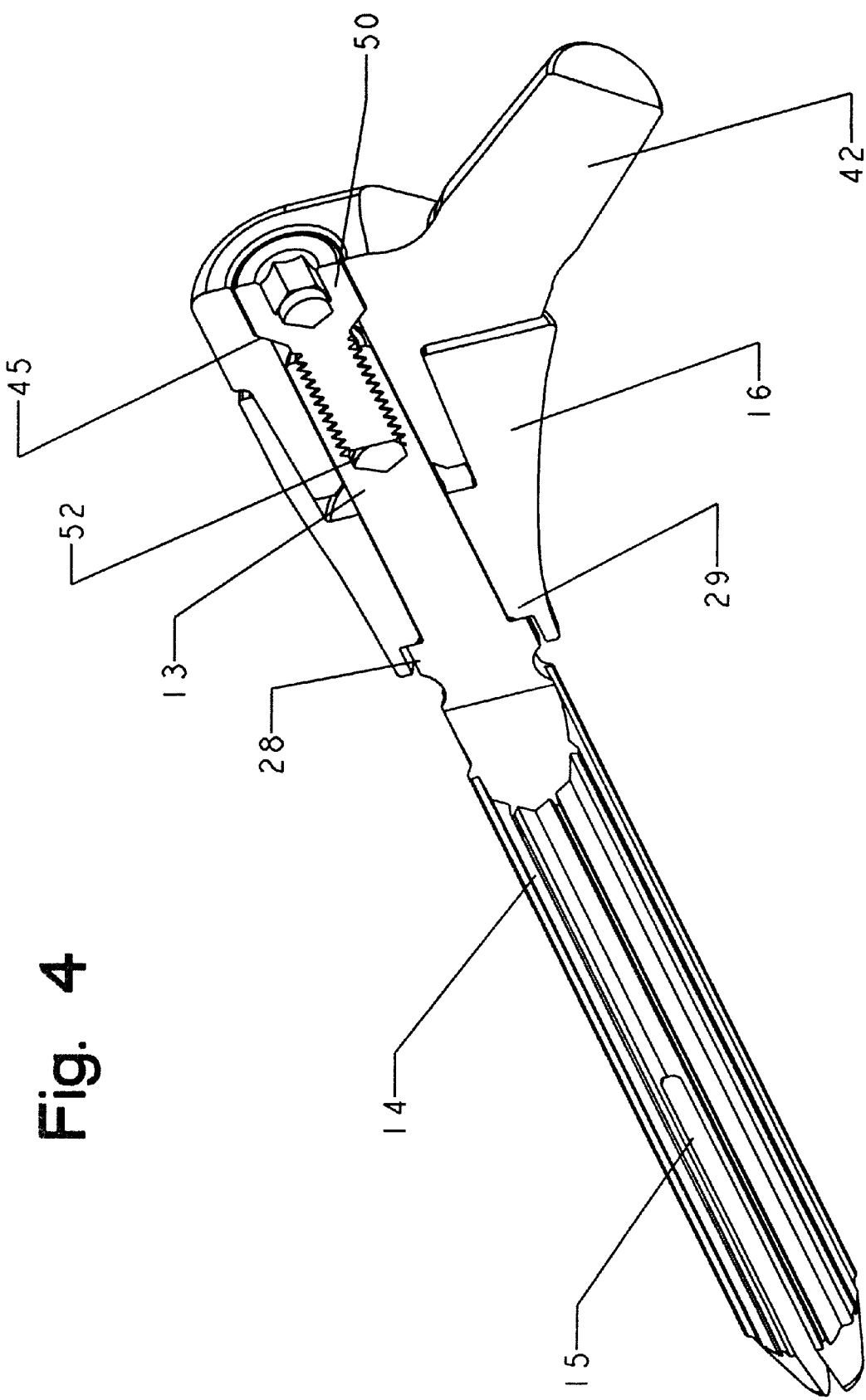
FIG. 4 shows another embodiment of the prosthesis of this invention partly in cross section and partly in elevation.

The prosthesis 10, shown in FIG. 1, has an intramedullary rod 11 which provides stability. The rod has a distal end 12 and a proximal end 13. The proximal end of the rod is smaller in diameter than the distal end. The distal end 12 is inserted into the patient's femur and forms the supporting connection for the entire prosthesis. The distal end of the rod may have flutes 14 (shown in FIG. 4) to increase the surface area of the junction between the rod and the intramedullary canal of the femur. The distal end of the rod may also have a slot 15 (shown in FIG. 4) along the longitudinal axis of the rod to better accommodate the internal anomalies occurring in the interior of the intramedullary canal. This structure allows the distal end of the rod to compress to a smaller diameter to more easily reach the desired depth of insertion.

Figure 2:
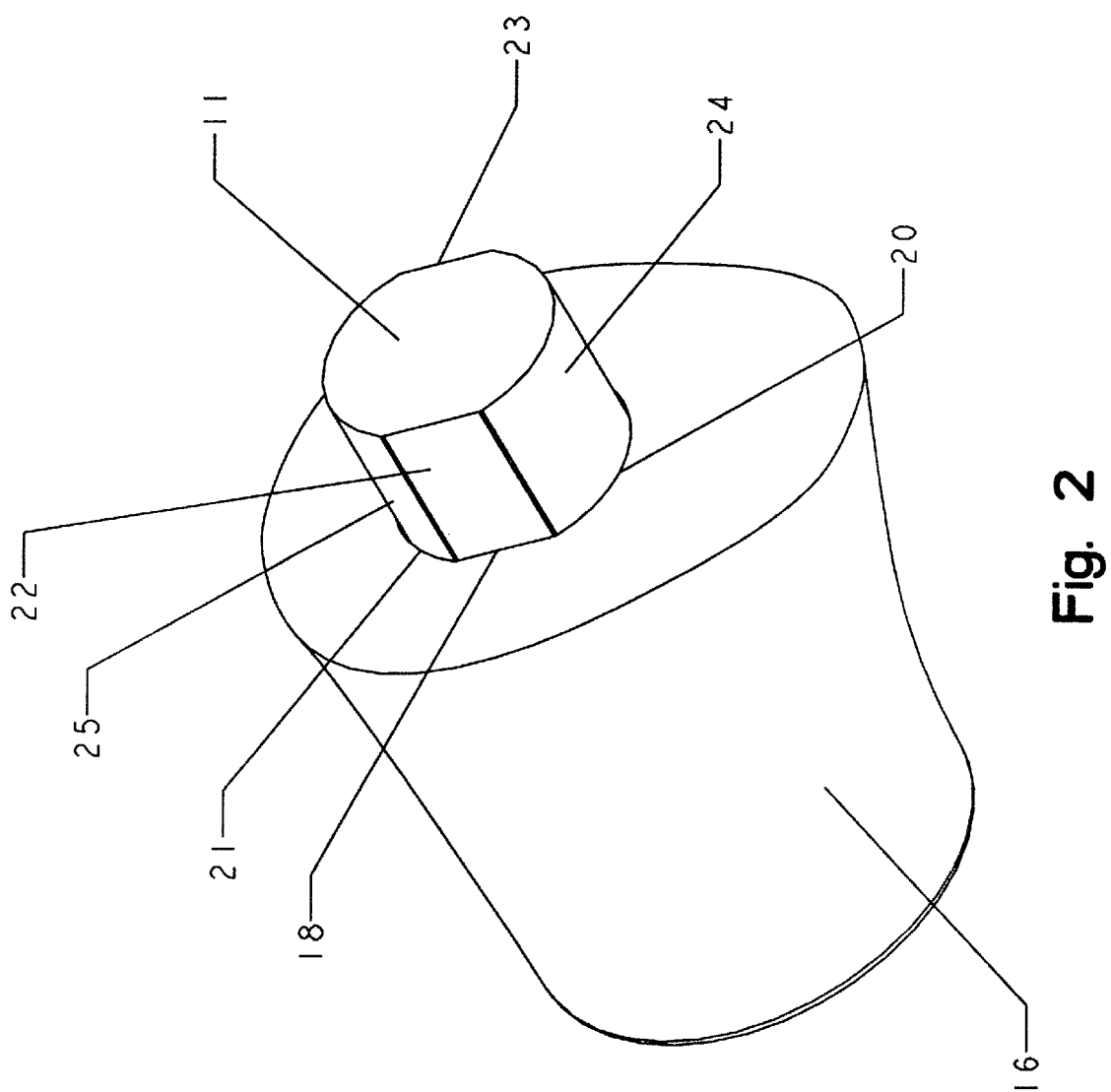
FIG. 2 shows an elevation of the proximal end of the intramedullary rod inserted through the distal end of the trochanter element along line 2—2 of FIG. 1.

The trochanter element 16 is mounted on the proximal end of the intramedullary rod. The trochanter has a through bore portion 17 in the distal end thereof through which the proximal end 13 of the intramedullary rod is inserted. As shown in FIG. 2, the through bore portion 17 and the proximal end 13 of the intramedullary rod have corresponding mating surfaces which lock the elements together preventing any rotational movement. The bore portion 17 has planar opposite sides 18 and 19 and curved surfaces 20 and 21 joining the ends of the planar sides. The proximal end of the intramedullary rod is sized to closely fit within the bore portion 17. The proximal end of the intramedullary rod also has opposite planar sides 22 and 23 joined by curved surfaces 24 and 25.

Because the intramedullary rod 11 and trochanter 16 do not move rotationally, it is very important that the orientation of the proximal end of the rod be established during insertion of the rod into the femur. Intramedullary rod 11 provides stability and the trochanter 16 acts as the load bearing element and may be provided in different lengths. The proper insertion of the rod allows the immovable connection of the trochanter to the intramedullary rod in the approximate original position of the excised head of the femur.

In addition to the complementary surfaces in portion 17 and the proximal end 13 of the intramedullary rod, the bore portion 17 may be formed with a taper 26 which is smaller toward the proximal end of the trochanter and larger at the distal end. The proximal end of the intramedullary rod may be formed with a slightly larger diameter taper 27 having a smaller end toward the proximal end. As the two elements are telescoped together, the tapered walls engage each other further strengthening the connection between the elements.

In another embodiment, the proximate end of the intramedullary rod carries a circumferential shoulder 28 which engages a seating face 29 formed about the through bore portion 17.

Either the cooperating tapers 26 and 27 or the shoulder 28 and seating face 29 establish a precise limit to the distance the trochanter may be telescoped over the intramedullary rod. This limit, in turn, establishes the overall length of the two elements.

The proximate end of the intramedullary rod has a threaded bore 52 for receiving the threaded end of bolt 50.

The proximal end of trochanter 16 has a through bore portion 30 which has a greater diameter than the diameter of the through bore portion 17 in the distal end. Through bore portion 30 receives the distal end 31 of the neck element 40. This through bore portion 30 may be cylindrical or conical.

Figure 3:
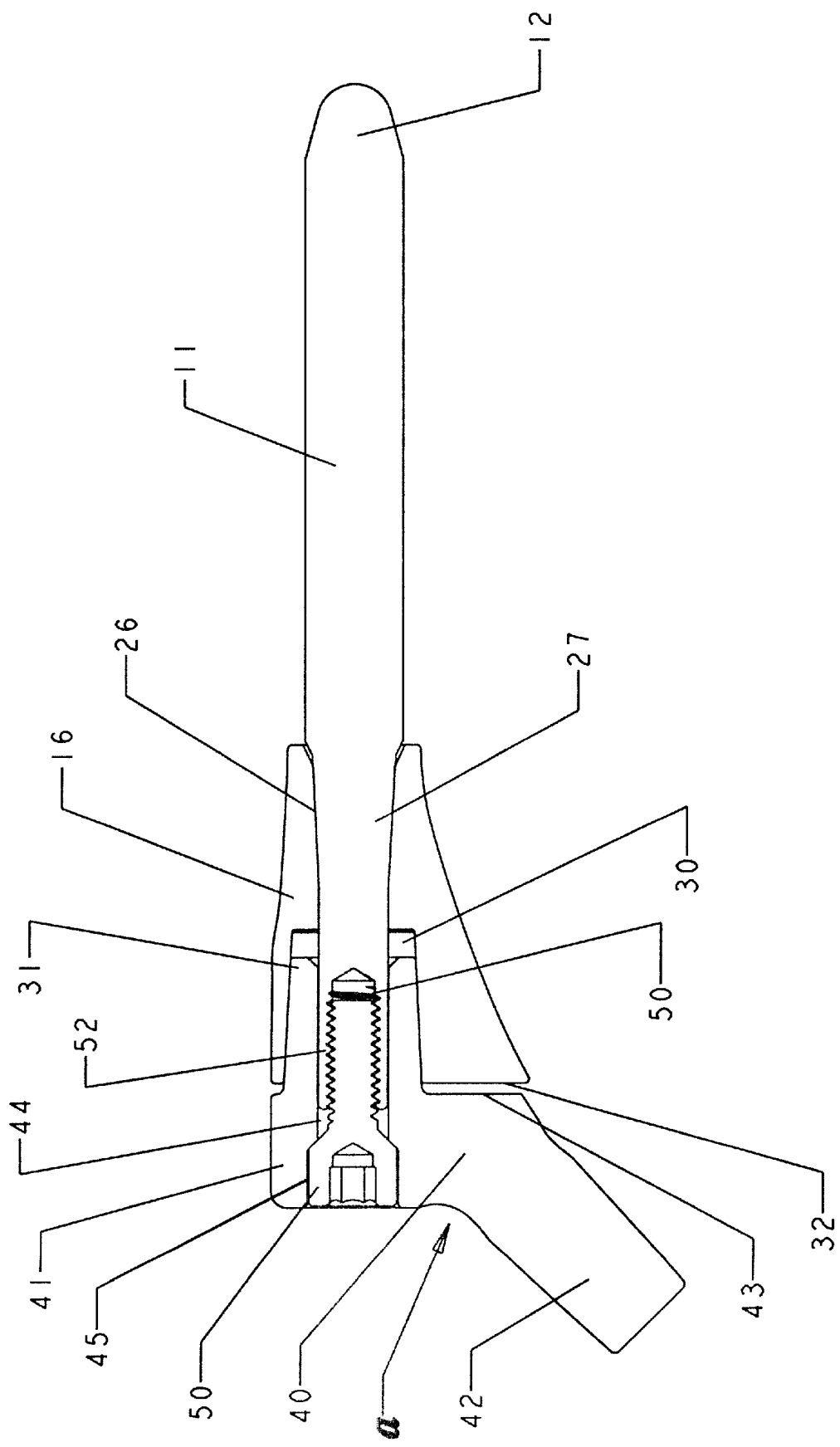
FIG. 3 is a cross section of another embodiment of the prosthesis of this invention.

If conical, the walls of the bore portion 30 taper from a large diameter proximal end toward the distal end. In the embodiment shown in FIG. 3, the trochanter bore has a taper in bore portion 17 and bore portion 30.

The through bore portion 30 establishes a rotationally adjustable connection with the neck 40. In this manner, the prosthesis may be adjusted, after the intramedullary rod has been inserted into the femur, to approximate the natural location of the original ball.

The trochanter is shaped like the natural femur head and has an outer diameter that is slightly larger than the intramedullary rod at the distal end. The distal end of the trochanter may, or may not, be partially inserted into the intramedullary canal. The body of the trochanter flares to a larger diameter proximal end which has a planar surface 32 containing the bore portion 30.

The neck 40 has a partially cylindrical body 41 with a laterally extending arm having an antiversion angle a from the proximal surface of the body 41. This arm carries the ball joint (not shown) for an artificial hip and can be specifically set at different angles.

The distal surface of the neck is formed as a flat surface 43 with a depending smaller diameter distal end 31. The distal end 31 is telescoped into the through bore portion 30 of the trochanter. The outer surface of the distal end may be cylindrical or conical. The conical surface of the distal end 31 tapers from a smaller distal end toward the surface 43. The base of the conical pin is slightly larger than the through bore portion 30 so that a friction fit is established when the elements are telescoped together. This maintains the rotational relationship between the elements.

The neck has a bore 44 extending from the proximal end through the distal end 31. The proximal end 45 of the bore 44 is countersunk to receive the head of the bolt 50. The distal end of bore 44 receives the proximal end 13 of the intramedullary rod 11.

The prosthesis is assembled by driving the threads of the bolt 50 into the threads 52 of the intramedullary rod. As these cooperating screw threads tighten, the elements of the prosthesis are drawn together forcing the tapered distal end of the neck into a friction fit with the tapered bore of the trochanter and the trochanter to a stop limit with the intramedullary rod. In the final disposition, the trochanter and the intramedullary rod a locked together over a major part of the length of each. And the neck is locked to the rotationally immovable trochanter over a major part of the length of each.

The various elements or components of the prosthesis may be made in different external sizes so that a range of elements is available to meet the size needs of various patients. However, the interconnecting portions of the different sized components are of the same size or, at least, made in a range of sizes so that the different external sized elements may be securely connected as described above.

What is claimed is:

1. A modular prosthesis to be used in hip replacement comprising:

an intramedullary rod, a trochanter and a neck, said intramedullary rod having a distal end adapted for insertion into the intramedullary canal of the femur and a proximal end, said proximal end having a circumference with opposite planar surfaces joined by curved surfaces, said proximal end having a screw threaded blind bore along a longitudinal axis of said intramedullary rod, said trochanter having a narrow distal end and a larger proximal end with a through bore from said distal end to said proximal end, said proximal end of said through bore having a smooth circumference, said distal end of said through bore having a circumference with opposite planar sides joined by curved surfaces, said circumference of said trochanter bore and said circumference of said proximal end of said intramedullary rod adapted to telescope together forming a rotationally secure connection, said neck having a distal end adapted to be inserted into the proximal end of said through bore of said trochanter, said distal end of said neck having a smooth circumference, said distal end of said neck and said proximal end of said through bore in said trochanter adapted to telescope together forming a rotationally adjustable connection, said neck having a through bore, said proximal end of said through bore having a countersunk bore, said distal end of said through bore adapted to telescope over the proximal end of said intramedullary rod, and a screw threaded bolt adapted to be disposed in said countersunk bore and threadably engaged with said screw threads in said proximal end of said intramedullary rod forming a locked integral prosthesis.

2. A modular prosthesis as claimed in claim 1 wherein said intramedullary rod has a circumferential shoulder, said trochanter has a circumferential seating face, said shoulder and said seating face forming a stop limit when said intramedullary rod and said trochanter are telescoped together.

3. A modular prosthesis as claimed in claim 1 wherein said distal end of said through bore in said trochanter has a tapered surface and said proximal end of said intramedullary rod has a tapered surface, said tapered surfaces forming a stop limit when said intramedullary rod and said trochanter are telescoped together.

4. A modular prosthesis as claimed in claim 3 wherein said distal end of said neck and said proximal end of said through bore in said trochanter each have complementary tapered surfaces, said complementary tapered surfaces forming a secure connection between said neck and said trochanter when said bolt is disposed in said proximal end of said intramedullary rod.

5. A modular prosthesis as claimed in claim 1 wherein said distal end of said neck and said proximal end of said through bore in said trochanter each have complementary tapered surfaces forming a secure connection between said neck and said trochanter when said bolt is disposed in said proximal end of said intramedullary rod.

6. A modular prosthesis as claimed in claim 1, 2, 3, 4, or 5 wherein said distal end of said intramedullary rod is fluted.

7. A modular prosthesis as claimed in claim 6 wherein said distal end of said intramedullary rod is slotted.

* * * * *